United States Patent [19]

Mueller et al.

[11] Patent Number: 5,302,620
[45] Date of Patent: Apr. 12, 1994

[54] BISGUANIDINES AND FUNGICIDES CONTAINING THEM

[75] Inventors: Thomas Mueller, Hessheim; Matthias Zipplies, Hirschberg; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 49,439

[22] Filed: Apr. 20, 1993

Related U.S. Application Data

[62] Division of Ser. No. 743,160, Aug. 9, 1991, Pat. No. 5,242,948.

[30] Foreign Application Priority Data

Aug. 22, 1990 [DE] Fed. Rep. of Germany ....... 4026473

[51] Int. Cl.$^5$ ................. A61K 31/155; C07C 279/16
[52] U.S. Cl. .................................... 514/635; 564/235; 564/238; 564/239
[58] Field of Search ................ 514/635; 564/235, 238, 564/239

[56] References Cited

U.S. PATENT DOCUMENTS 3,468,898  9/1969  Cutler et al. .................... 544/299

OTHER PUBLICATIONS

McKay et al., J. Med. Chem., 6, 587–595, 1963.

*Primary Examiner*—Mukund J. Shah
*Assistant Examiner*—Y. N. Gupta
*Attorney, Agent, or Firm*—Oblon, Spivak, McClelland, Maier & Neustadt

[57] ABSTRACT

The present invention relates to bisguanidine derivatives of the formula I

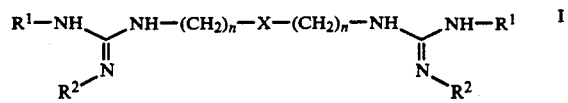

where
$R^1$ and $R^2$ are each, independently of one another, hydrogen, alkyl, alkenyl, alkynyl, alkoxyalkyl, haloalkenyl; or cycloalkyl which has 5–12 carbon atoms in the ring and may be substituted, or benzyl which may be substituted, with the proviso that only one of $R^1$ and $R^2$ can be hydrogen; or
$R^1$ and $R^2$ are, together with the atoms which they substitute, a heterocyclic ring which may be substituted;
X is $CH_2$, O, a single bond, NH, N-alkyl or N-benzyl whose phenyl ring may be substituted,
n is 5 to 8, and their plant-compatible acid addition salts and their metal complexes and fungicides containing these compounds.

8 Claims, No Drawings

BISGUANIDINES AND FUNGICIDES CONTAINING THEM

This is a division of application Ser. No. 07/743,160 filed on Aug. 9, 1991 now U.S. Pat. No. 5,242,948.

The present invention relates to novel bisguanidines with a fungicidal action and to fungicides containing them.

GB 1,114,155 discloses the compound

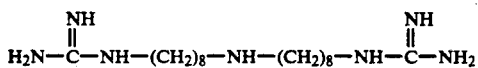

and its fungicidal action.

Also known to have a fungicidal action are α,ω-bis(3,4-dichlorobenzylguanidino)alkanes (A. F. McKay et al., J. Med. Chem. 6 (1963) 587).

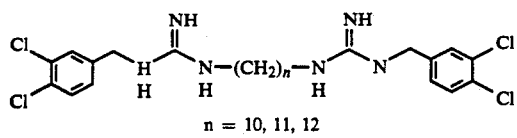

Other guanidinas are known from U.S. Pat. No. 3,488,898, DE 39 22 232.2, EP 338,430, G.B. 935,614 and EP 406,899. However, the action of these compounds is not always satisfactory, especially at low application rates and concentrations.

We have now found that bisguanidine derivatives of the formula I

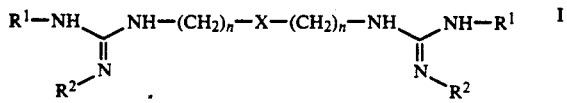

where $R^1$ and $R^2$ are each, independently of one another, hydrogen, $C_5$–$C_{10}$-alkyl, $C_3$–$C_{10}$-alkenyl, $C_3$–$C_{10}$-alkynyl, $C_1$–$C_8$-alkoxy-$C_2$–$C_8$-alkyl, $C_3$–$C_{10}$-haloalkenyl; or cycloalkyl which has 5–12 carbon atoms in the ring and can carry up to three of the following substituents: hydroxyl, $C_1$–$C_{10}$-alkyl, $C_1$–$C_{10}$-alkoxy, $C_1$–$C_{10}$-haloalkyl and $C_1$–$C_8$-alkoxy-$C_1$–$C_8$-alkyl; or benzyl which can be substituted up to three times by $C_1$–$C_{10}$-alkyl or $C_1$–$C_{10}$-alkoxy, it being possible for the substituent also to carry a hydroxyl or $C_1$–$C_6$-alkoxy group; or the benzyl is substituted by $C_1$–$C_{10}$-haloalkyl, with the proviso that only one of $R^1$ and $R^2$ can be hydrogen; or $R^1$ and $R_2$ are, together with the atoms which they substitute, a 5- to 11-membered heterocyclic ring which can be substituted once to three times by $C_1$–$C_{10}$-alkyl or $C_1$–$C_8$-alkoxy-$C_1$–$C_8$-alkyl;

X is $CH_2$, O, a single bond, NH, N-($C_1$–$C_{10}$-alkyl) or N-benzyl whose phenyl can be substituted once to three times by $C_1$–$C_{10}$-alkyl, $C_1$–$C_{10}$-alkoxy, $C_1$–$C_{10}$-haloalkyl n is 5 to 8, and their plant-compatible acid addition salts and their metal complexes, have an excellent fungicidal action against phytopathogenic fungi.

If $R^1$ or $R^2$ is hydrogen, the compounds can exist in tautomeric forms which are covered by the invention.

With a view to their fungicidal action, the preferred compounds are those in which the substituents have the following meanings:

$R^1$, $R^2$ hydrogen, with the proviso that not less than one of $R^1$ and $R^2$ is different from hydrogen; $C_5$–$C_{10}$-alkyl, especially pentyl, 1,1-dimethylpropyl or 2,4,4-trimethyl-2-pentyl; $C_3$–$C_{10}$-alkenyl or $C_3$–$C_{10}$-alkynyl, especially allyl, dimethylallyl or 2-butynyl; $C_1$–$C_8$-alkoxy-$C_2$–$C_8$-alkyl, especially methoxyethyl, tert.-butoxyethyl or methoxypropyl; $C_3$–$C_{10}$-haloalkenyl, especially 3-bromo-2-propenyl, 2-bromo-2-propenyl or 3-chloro-2-propenyl; cyclopentyl, cyclohexyl, cycloheptyl, cyclooctyl and cyclododecyl, it being possible for these to carry up to three of the following:
hydroxyl;

$C_1$–$C_{10}$-alkyl, especially methyl, ethyl, propyl, isopropyl, butyl, isobutyl, sec.-butyl, tert.-butyl, 1,1-dimethylpropyl or 2,4,4-trimethyl-2-pentyl;

$C_1$–$C_{10}$-alkoxy, especially methoxy, ethoxy, isopropoxy, n-butoxy, tert.-butoxy or octyloxy; $C_1$–$C_4$-haloalkyl, especially trifluoromethyl or pentafluoroethyl;

$C_1$–$C_8$-alkoxy-$C_1$–$C_8$-alkyl, especially methoxymethyl, ethoxymethyl, methoxyethyl, tert.-butoxymethyl or 1-methoxy-1-methylethyl; or benzyl, which can carry up to three of the following substituents:

$C_1$–$C_{10}$-alkyl, especially methyl, ethyl, propyl, isopropyl, butyl, isobutyl, sec.-butyl, tert.-butyl, 1,1-dimethylpropyl, 2,3-dimethylpropyl, 1,1,2-trimethylpropyl, 2-hydroxy-2-propyl or 2-methoxy-2-propyl;

$C_1$–$C_{10}$-alkoxy, especially methoxy, ethoxy, isopropoxy, n-butoxy, tert.-butoxy or octyloxy; $C_1$–$C_{10}$-haloalkyl, especially trifluoromethyl or pentafluoroethyl;

particularly preferred for $R^1$ and $R_2$ are hydrogen, with the proviso that not less than one of $R^1$ and $R^2$ is different from hydrogen, cyclopentyl, cyclohexyl, cycloheptyl, 2-methylcyclohexyl, 3-methylcyclohexyl, 3-trifluoromethylcyclohexyl, 3,3-dimethylcyclohexyl, 4-tert.-butylcyclohexyl, 4-methylbenzyl, 4-ethylbenzyl, 4-isopropylbenzyl, 4-tert.-butylbenzyl, 4-(1,1,2-trimethylpropyl)benzyl, 2,4-dimethylbenzyl, 4-methoxybenzyl, 4-tert.-butoxybenzyl or 3,4-dimethoxybenzyl;

$R^1$ and $R^2$ are, together with the atoms which they substitute, a 5- to 11-membered heterocyclic ring, especially an imidazolinyl, tetrahydropyrimidyl, tetrahydro-1,3-diazepinyl, hexahydro-1,3-diazocinyl or hexahydro-1,3-diazoninyl, it being possible for these to carry up to three of the following substituents:

$C_1$–$C_{10}$-alkyl, especially methyl, ethyl, propyl, isopropyl, butyl, isobutyl, sec.-butyl, tert.-butyl, 1,1-dimethylpropyl or 2,4,4-trimethyl-2-pentyl;

$C_1$–$C_8$-alkoxy-$C_1$–$C_8$-alkyl, especially methoxymethyl, ethoxymethyl, methoxyethyl, tert.-butoxymethyl or 1-methoxy-1-methylethyl;

particularly preferred for $R^1$ and $R^2$ are imidazolinyl, tetrahydropyrimidyl, 4,4-dimethyltetrahydropyrimidyl, 5-tert.-butyltetrahydropyrimidyl or 5-ethyl-5-propyl-hexahydro-1,3-diazocinyl X is $CH_2$, O, a single bond, NH, N-($C_1$–$C_{10}$-alkyl), especially N-methyl, N-ethyl, N-propyl, N-isopropyl, N-butyl, N-isobutyl, N-sec.-butyl, N-tert.-butyl or N-1,1-dimethylpropyl, N-benzyl whose phenyl can be substituted by $C_1$–$C_{10}$-alkyl, especially methyl, ethyl, propyl, isopropyl, butyl, isobutyl, sec.-butyl, tert.-butyl, 1,1-dimethylethyl, 1,1-dimethylpropyl, 2,3-dimethylpropyl, 1,1,2-trimethylpropyl, $C_1$–$C_{10}$-alkoxy, especially methoxy, ethoxy, isopropoxy, n-butoxy, tert.-butoxy or octyloxy, $C_1$–$C_{10}$-haloalkyl, especially trifluoromethyl or pentafluoroethyl, or halogen, especially fluorine, chlorine or bromine; particularly preferred for X are $CH_2$, NH, N-methyl, N-ethyl, N-benzyl, N-4-tert.-butyl-benzyl, N-4-(1,1,2-trimethylpropyl)benzyl, N-4-methoxybenzyl, N-4-tert.-butoxybenzyl, N-4-chlorobenzyl, N-4-fluorobenzyl or a single bond; n is 5 to S, i.e. 5, 6, 7 or 8.

Also preferred are compounds in which $R^1$ and $R^2$ are, independently of each other, hydrogen or cycloalkyl, as defined above, and X is NH. Compounds in which $R^1$ and $R^2$ together denote imidazolinyl or tetrahydropyrimidinyl and X is NH or a single bond are also preferred.

Suitable acid addition salts are the plant-compatible salts of those acids which do not impair the fungicidal action of I, e.g. iodides, chlorides, bromides, sulfates, dodecyl sulfates, nitrates, carbonates, phosphates, borates, formates, acetates, propionates, benzoates, oxalates, naphthalenesulfonates, dodecylbenzenesulfonates, lactates, citrates and the salts with the saccharin anion.

Suitable metal complexes are those of copper, zinc, tin, manganese, iron, cobalt or nickel. The complexes are preferably prepared from the free bases I and the salts with mineral acids, for example the chlorides or sulfates, of the metals.

The bisguanidines I can be prepared in a variety of ways, the following methods being preferred:

a) Preparation from Isothiuronium Salts and Diamines $$2 \begin{array}{c} R^1-NH \\ \phantom{2} \diagdown \\ \phantom{2} N \\ \phantom{2} \diagup \\ R^2 \end{array} \begin{array}{c} S-R^3 \\ \| \\ \phantom{N} \\ \phantom{N} \\ H \end{array} + Y'- \quad II$$

$$+ \quad H_2N-(CH_2)_n-X-(CH_2)_n-NH_2 \quad III \quad \longrightarrow \quad I.HY'$$

In these formulae, $R^3$ is benzyl or $C_1$-$C_4$-alkyl, e.g. methyl or ethyl, and Y, is chloride, bromide, iodide, sulfate, methosulfate, methanesulfonate or tosylate.

The starting compounds II and III are known or can be obtained in a known manner (for the isothiuronium salts, see Houben-Weyl, Methoden der Organischen Chemie, 4th edition, Vol. IX, pp. 900 et seq.).

The reaction of isothiuronium salts with diamines which is shown in the diagram and is known (e.g. A. V. Bogatskii et al., Khim.-Farm. Zh. 17 (1983) 308; CA 98 215574z) to give bisguanidine compounds I.HY' is preferably carried out in polar solvents such as alcohols, ketones, ethers, nitriles, dimethyl sulfoxide, N-methylpyrrolidone, dimethylformamide or dimethylacetamide.

The reaction is generally carried out with from 2.0 to 4.0 moles, particularly preferably 2.0 moles, of isothiuronium salt II per mole of diamine III. It is also possible to have a tertiary amine such as triethylamine present as additional base. In this case, equimolar amounts of additional base and of isothiuronium salt are preferably employed.

The reaction can be carried out at from 20° C. to the boiling point of the solvent, preferably from 60° to 130° C.

The reaction is preferably carried out under atmospheric pressure.

Anion exchange can be used to obtain salts with other anions or, by replacement by hydroxyl ions, the free bases I.

b) Preparation from Aminoiminomethanesulfonic Acids and Diamines $$2 \begin{array}{c} R^1-NH \\ \phantom{2} \diagdown \\ \phantom{2} N \\ \phantom{2} \diagup \\ R^2 \end{array} \begin{array}{c} SO_3H \\ \| \\ \phantom{N} \end{array} +$$

IV $$H_2N-(CH_2)_n-X-(CH_2)_n-NH_2 \quad \longrightarrow \quad I$$

III

The starting compounds IV are known or can be prepared from thiourea derivatives in a conventional manner (e.g. C. A. Maryanoff et al., J. Org. Chem., 51 (1986) 1882).

Suitable temperatures for the reaction are from 0° C. to the boiling point of the solvent.

The ratios of amounts and the pressure are the same as for method a).

The solvents are the same as for method a) but acetonitrile is very particularly preferred.

c) Preparation from Carbodiimides and Diamines $$\left. \begin{array}{c} 2\ R^1-N=C=N-R^2 \quad V \\ H_2N-(CH_2)_n-X-(CH_2)_n-NH_2 \quad III \end{array} \right\} \longrightarrow I$$

The starting compounds V are known or can be prepared by known processes (cf. e.g. M. Mikolaiczyk, Tetrahedron 37 (1981) 233).

It is advisable to employ for the reaction 2 moles of carbodiimide V per mole of diamine III, but it is preferable to use a small excess of amine or carbodiimide, of up to about 10%, over the 1:2 ratio.

Suitable solvents for the reactions are hydrocarbons such as hexane or toluene, short-chain alcohols such as isopropanol or tert.-butanol, amides such as dimethylformamide or nitriles such as acetonitrile.

The temperature and the pressure are the same as for method a).

d) Preparation from Imidocarbonates and Amines

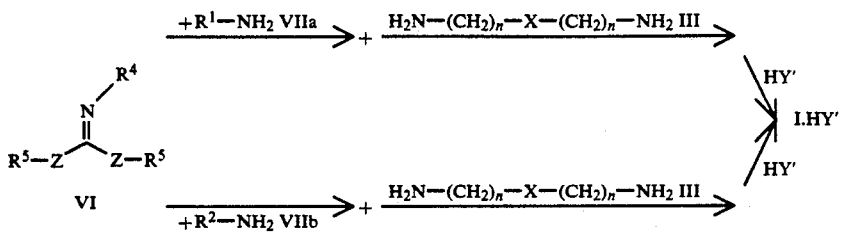

When Z=O in this formula, $R^4$ is cyano, benzoyl or methanesulfonyl, and $R^5$ is phenyl, and when Z=S, $R^4$ is cyano and $R^5$ is methyl.

The reaction of imidocarbonates with two amines is known (cf. e.g. A. Buschauer, Arzneim.-Forsch./Drug. Res., 37 (1987) 1003, 1008; Arch. Pharm., 321 (1988) 281) and is carried out in two separate stages. The imidocarbonate is preferably reacted with the first amine in a chlorohydrocarbon such as dichloromethane, an ether such as diethyl ether or tetrahydrofuran, a short-chain alcohol such as methanol or isopropanol, a water/alcohol mixture such as water/methanol or a nitrile such as acetonitrile. The reaction of the product with the second amine is then carried out in a polar solvent such as methanol, ethanol, isopropanol, tert.-butanol, pyridine or acetonitrile.

It is advisable to employ for the reactions 1.0 mole of amine VIIa or VIIb and 0.5 mole of diamine III per mole of imidocarbonate VI, but a small excess of amine, of up to about 10%, is preferably used.

The temperature and pressure are the same as for method a). The resulting compounds are hydrolyzed in a conventional manner, advantageously in a mineral acid or an organic carboxylic acid at, for example, 70° to 120° C. Preferably used is 2 to 10M hydrochloric acid or 50 to strength acetic acid.

The chlorides or acetates of the compounds I with $R^1$ or $R^2$ equal to hydrogen are obtained.

The free bases I are prepared as in method a).

e) Preparation from Cyanogen Bromide and Amines

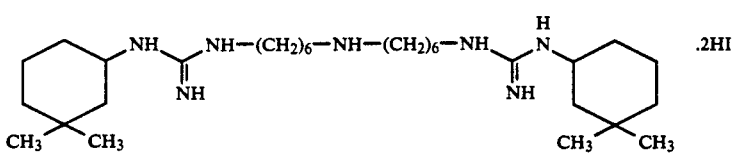

Y' in these formulae is preferably chloride.

The reaction of cyanogen bromide with amines, which is known from Houben-Weyl, Methoden der Org. Chemie, 4th edition, Vol. E4, p. 981, to give N-substituted cyanamides is preferably carried out in a two-phase system, e.g. water/dichloromethane, or else anhydrous in inert solvents such as diethyl ether, tetrahydrofuran, dioxane, dichloromethane or toluene. The reactions are preferably carried out at from −20° to +10° C.

The ratios of amounts and the pressure are the same as for method d).

The reaction of the N-substituted cyanamides VIIIa, VIIIb and IX, which is known from Houben-Weyl, Methoden der Org. Chemie, 4th edition, Vol. E4, p. 609, with the hydrochlorides of the amines III, VIIa and VIIb is preferably carried out without solvent at, for example, from 130° to 250° C.

The amounts, the pressure and the preparation of the free bases I are the same as for method d).

The compounds I with $R^1$ or $R^2$ equal to hydrogen are obtained.

The compounds of the formula I and the salts and metal complexes thereof are suitable as fungicides and are well tolerated by plants.

PREPARATION EXAMPLES

Example 1

Method a) (Compound 11a)

1,13-Bis(3,3-dimethylcyclohexylguanidino)-7-azatridecane dihydroiodide

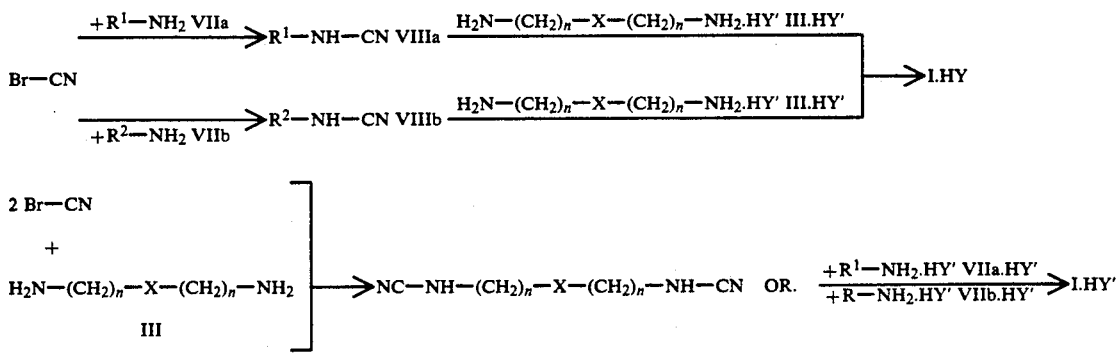

A mixture of 16.4 g (0.050 mol) of 3,3-dimethylcyclohexyl-S-methylisothiuronium iodide, 5.3 g (0.025 mol) of 1,13-diamino-7-azatridecane, 5 g (0.050 mol) of triethylamine and 15 g of molecular sieves (4 Å) in 200 ml of anhydrous acetonitrile was refluxed under a nitrogen atmosphere for 48 hours, with elimination of methanethiol. The mixture was filtered hot and the compound was isolated from the solution.

Yield: 93% of theory; melting point 120° C.

Precursor A1

3,3-Dimethylcyclohexyl-S-methylisothiuronium iodide

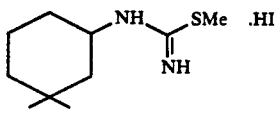

A solution of 63 g (0.339 mol) of 3,3-dimethylcyclohexylthiourea and 48.1 g (0.339 mol) of iodomethane in 100 ml of methanol was refluxed for 1 hour. The solvent was distilled out under reduced pressure to leave a yellow resinous solid.

Yield: 58% of theory, melting point 80° C.

Precursor A2

3,3-Dimethylcyclohexylthiourea

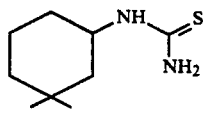

59 g (0.42 mol) of benzoyl chloride were added dropwise over the course of 10 minutes to a solution of 33 g (0.44 mol) of ammonium thiocyanate in 100 ml of absolute acetone. The mixture was refluxed for 10 minutes and then 50.8 g (0.40 mol) of 3,3-dimethylcyclohexylamine were added dropwise, and the mixture was refluxed for a further 20 minutes and then stirred into 500 ml of ice-water. The precipitated solid was filtered off with suction, washed with water, dissolved in a hot mixture of 500 ml of 10% strength sodium hydroxide solution and 125 ml of ethanol and refluxed for 30 minutes. The reaction mixture was then diluted with ice-water, and the pH was initially adjusted to 1 with concentrated hydrochloric acid and then to 9 with solid sodium bicarbonate. The resulting precipitate was filtered off with suction, washed with water and dried at 80° C. under reduced pressure.

Yield: 85% of theory; melting point 153° C.

Example 2

(Compound 18a)

1,17-Biscyclohexylguanidino-9-azaheptadecane triacetate

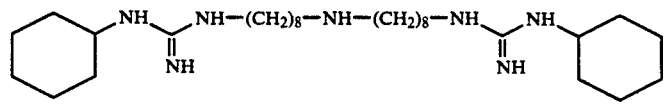

10.2 g (0.011 mol) of 1,17-biscyclohexylguanidino-9-azaheptadecane dihydroiodide in 150 ml of methanol/water (1:1) were filtered through a column containing 250 g of ion exchanger (OH⁻ form). The free guanidine base obtained after working up was dissolved in methanol and converted into the triacetate with excess glacial acetic acid.

Example 3

Method a) (Compound 16a)

1,17-Biscyclohexylguanidino-9-azaheptadecane dihydroiodide

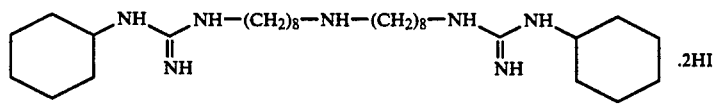

A mixture of 30.0 g (0.10 mol) of cyclohexyl-S-methylisothiuronium iodide, 13.6 g (0.05 mol) of 1,17-diamino-9-azaheptadecane, 10.0 g (0.10 mol) of triethylamine and 20 g of molecular sieves (4 Å) in 300 ml of anhydrous acetonitrile was refluxed under a nitrogen atmosphere for 5 days, methanethiol being eliminated. The mixture was filtered hot and worked up as usual.

Yield: 43% of theory; melting point 170° C.

Precursor B1

Cyclohexyl-S-methylisothiuronium iodide

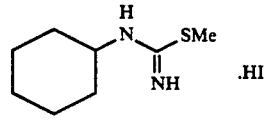

A solution of 62.0 g (0.392 mol) of cyclohexylthiourea and 55.7 g (0.392 mol) of iodomethane in 300 ml of methanol was refluxed for 1 hour. After cooling to room temperature, the product was precipitated by adding methyl tert.-butyl ether, filtered off with suction, washed with methyl tert.-butyl ether and hexane and finally dried at 50° C. under reduced pressure.

Yield: 68% of theory; melting point 115°–120° C.

Precursor B2

Cyclohexylthiourea

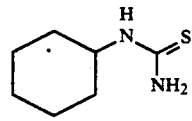

295.5 g (2.1 mol) of benzoyl chloride were added dropwise over the course of 10 minutes to a solution of 165.0 g (2.2 mol) of ammonium thiocyanate in 500 ml of absolute acetone. After refluxing for 10 minutes, 198.9 g (2.0 mol) of cyclohexylamine were added dropwise, and the mixture was refluxed for a further 20 minutes. It was then stirred into 4 l of ice-water, and the water was decanted off the oily product. The residue was dissolved in a hot mixture of 2 l of 10% strength sodium hydroxide solution and 500 ml of ethanol and refluxed for 30 minutes. The reaction mixture was then diluted with ice-water, and the pH was adjusted initially to 1 with concentrated hydrochloric acid and then to 9 with solid sodium bicarbonate. The resulting precipitate was filtered off with suction, washed with water and dried at 80° C. under reduced pressure.

Yield: 78% of theory; melting point 135° C.

Example 4

Method c) (Compound 14a)

1,13-Bis(N,N'-dicyclohexylguanidino)-7-azatridecane trihydrochloride

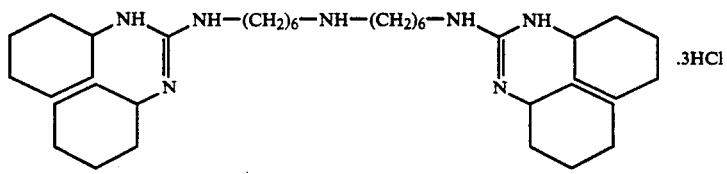

A mixture of 49.4 g (0.24 mol) of dicyclohexylcarbodiimide, 21.5 g (0.10 mol) of 1,13-diamino-7-azatridecane and 400 ml of anhydrous tert.-butanol was refluxed for 12 hours. The isolated oily product was mixed with methanolic hydrochloric acid and the solvent was removed by distillation under reduced pressure, leaving a colorless solid.

Yield: 26% of theory; melting point 140° C.

Example 5

(Compound 35b)

1,12-Bis(2-amino-3,4,5,6-tetrahydropyrimidyl)dodecane diacetate

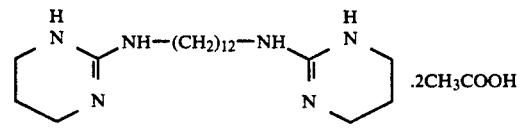

30.0 g 10.048 mol) of 1,12-bis(2-amino-3,4,5,6-tetrahydropyrimidyl)dodecane dihydroiodide in 300 ml of methanol/water (1:1) were filtered through a column containing 250 g of ion exchanger (OH− form). The free guanidine base obtained after working up was dissolved in methanol and converted into the diacetate with excess glacial acetic acid.

Example 6

Method a) (Compound 34b)

1,12-Bis(2-amino-3,4,5,6-tetrahydropyrimidyl)dodecane dihydroiodide

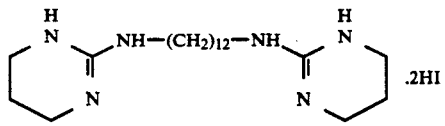

A mixture of 103.3 g (0.4 mol) of 2-S-methyl-3,4,5,6-tetrahydropyrimidinium iodide, 40.0 g (0.2 mol) of 1,12-diaminododecane, 20.2 g (0.2 mol) of triethylamine and 60 g of molecular sieves (4 Å) in 1 l of anhydrous acetonitrile was refluxed under a nitrogen atmosphere for 16 hours, with elimination of methanethiol. The mixture was filtered hot and then worked up as Yield: 81% of theory of a brown oil
IR (film): 3217, 2925, 2853, 1642, 1315 cm⁻¹

Precursor D1

2-S-Methyl-3,4,5,6-tetrahydropyrimidylisothiuronium iodide

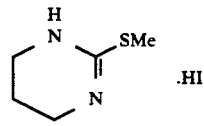

A solution of 50.0 g (0.431 mol) of perhydropyrimidinethione and 61.2 g (0.431 mol) of iodomethane in 200 ml of methanol was refluxed for 1 hour. After cooling to room temperature, the product was precipitated by adding methyl tert.-butyl ether, filtered off with suction, washed with methyl tert.-butyl ether and dried.

Yield 94% of theory; melting point 135° C.

TABLE 1

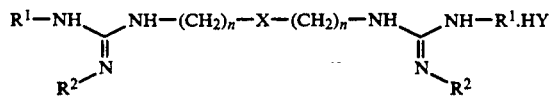

| Comp. No. | R¹ | R² | X | n | HY | m.p./IR (film) [cm⁻¹] |
|---|---|---|---|---|---|---|
| 1a | Cyclohexyl | H | NH | 6 | HCl | 125° C. |
| 2a | Cyclohexyl | H | NH | 6 | CH₃COOH | 100° C. |
| 3a | Cyclohexyl | H | NH | 6 | C₂H₂O₄ | 140° C. |
| 4a | Cyclohexyl | H | NH | 6 | — | |
| 5a | Cyclopentyl | H | NH | 6 | — | |
| 6a | Cyclooctyl | H | NH | 6 | — | |
| 7a | Cyclododecyl | H | NH | 6 | — | |
| 8a | 4-tert.-Butylcyclohexyl | H | NH | 6 | — | |
| 9a | 4-Isopropylcyclohexyl | H | NH | 6 | — | |
| 10a | 3-Trifluoromethylcyclohexyl | H | NH | 6 | — | |
| 11a | 3,3-Dimethylcyclohexyl | H | NH | 6 | HI | 120° C. |

TABLE 1-continued

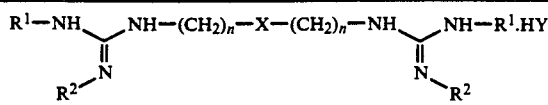

| Comp. No. | R¹ | R² | X | n | HY | m.p./IR (film) [cm$^{-1}$] |
|---|---|---|---|---|---|---|
| 12a | Cyclohexyl | Cyclohexyl | NH | 6 | — | 2926, 2851, 1639, 1448, |
| 13a | Cyclohexyl | Cyclohexyl | NH | 6 | CH$_3$COOH | 3205, 3085, 2930, 2855, 1612, 1573, 1450, 1400, 1366, 1246 |
| 14a | Cyclohexyl | Cyclohexyl | NH | 6 | HCl | 140° C. |
| 15a | Cyclohexyl | H | NH | 8 | — | 3279, 3185, 2929, 2854, 1652 |
| 16a | Cyclohexyl | H | NH | 8 | HI | 170–172° C. |
| 17a | Cyclohexyl | H | NH | 8 | HCl | 110° C. |
| 18a | Cyclohexyl | H | NH | 8 | CH$_3$COOH | 98–100° C. |
| 19a | Cyclohexyl | H | NH | 8 | C$_2$H$_2$O$_4$ | 165–167° C. |
| 20a | Cyclopentyl | H | NH | 8 | — | |
| 21a | Cyclooctyl | H | NH | 8 | — | |
| 22a | Cyclododecyl | H | NH | 8 | — | |
| 23a | 4-tert.-Butylcyclohexyl | H | NH | 8 | — | |
| 24a | 4-Isopropylcyclohexyl | H | NH | 8 | — | |
| 25a | 3-Trifluoromethylcyclohexyl | H | NH | 8 | — | |
| 26a | 3,3-Dimethylcyclohexyl | H | NH | 8 | — | |
| 27a | Cyclohexyl | Cyclohexyl | NH | 8 | — | |
| 28a | Cyclohexyl | H | single bond | 5 | | |
| 29a | Cyclopentyl | H | single bond | 5 | | |
| 30a | Cyclooctyl | H | single bond | 5 | | |
| 31a | Cyclododecyl | H | single bond | 5 | — | |
| 32a | 4-tert.-Butylcyclohexyl | H | single bond | 5 | — | |
| 33a | 4-Isopropylcyclohexyl | H | single bond | 5 | — | |
| 34a | 3-Trifluoromethylcyclohexyl | H | single bond | 5 | — | |
| 35a | 3,3-Dimethylcyclohexyl | H | single bond | 5 | — | |
| 36a | Cyclohexyl | Cyclohexyl | single bond | 5 | — | |
| 37a | Cyclohexyl | H | CH$_2$ | 5 | — | |
| 38a | Cyclopentyl | H | CH$_2$ | 5 | — | |
| 39a | Cyclooctyl | H | CH$_2$ | 5 | — | |
| 40a | Cyclododecyl | H | CH$_2$ | 5 | — | |
| 41a | 4-tert.-Butylcyclohexyl | H | CH$_2$ | 5 | — | |
| 42a | 4-Isopropylcyclohexyl | H | CH$_2$ | 5 | — | |
| 43a | 3-Trifluoromethylcyclohexyl | H | CH$_2$ | 5 | — | |
| 44a | 3,3-Dimethylcyclohexyl | H | CH$_2$ | 5 | — | |
| 45a | Cyclohexyl | Cyclohexyl | CH$_2$ | 5 | — | |
| 46a | Cyclohexyl | H | single bond | 6 | — | |
| 47a | Cyclopentyl | H | single bond | 6 | — | |
| 48a | Cyclooctyl | H | single bond | 6 | — | |
| 49a | Cyclododecyl | H | single bond | 6 | — | |
| 50a | 4-tert.-Butylcyclohexyl | H | single bond | 6 | — | |
| 51a | 4-Isopropylcyclohexyl | H | single bond | 6 | — | |
| 52a | 3-Trifluoromethylcyclohexyl | H | single bond | 6 | — | |
| 53a | 3,3-Dimethylcyclohexyl | H | single bond | 6 | — | |
| 54a | Cyclohexyl | Cyclohexyl | single bond | 6 | — | |
| 55a | p-tert.-Butylbenzyl | H | NH | 6 | — | |
| 56a | p-tert.-Butylbenzyl | Butyl | NH | 6 | — | |
| 57a | p-tert.-Butylbenzyl | Cyclohexyl | NH | 6 | — | |
| 58a | p-(1,1,2-Trimethylpropyl)benzyl | H | NH | 6 | — | |
| 59a | p-(1,1,2-Trimethylpropyl)-benzyl | Cyclooctyl | NH | 6 | — | |
| 60a | p-tert.-Butoxybenzyl | H | NH | 6 | — | |
| 61a | p-tert.-Butoxybenzyl | Cyclohexyl | NH | 6 | — | |
| 62a | p-tert.-Butylbenzyl | H | NH | 8 | — | |
| 63a | p-tert.-Butylbenzyl | Cyclohexyl | NH | 8 | — | |
| 64a | p-tert.-Butylbenzyl | Cyclooctyl | NH | 8 | — | |
| 65a | p-Isopropylbenzyl | H | NH | 8 | — | |
| 66a | p-Isopropylbenzyl | 1,3-Dimethyl-butane | NH | 8 | — | |
| 67a | p-Methoxybenzyl | H | NH | 8 | — | |
| 68a | p-Methoxybenzyl | Propyl | NH | 8 | — | |
| 69a | p-tert.-Butylbenzyl | H | single bond | 5 | — | |
| 70a | p-tert.-Butylbenzyl | Cyclohexyl | single bond | 5 | — | |
| 71a | p-Ethoxybenzyl | H | single bond | 5 | — | |
| 72a | p-Ethoxybenzyl | Isopropyl | single bond | 5 | — | |
| 73a | p-tert.-Butylbenzyl | H | CH$_2$ | 5 | — | |
| 74a | p-tert.-Butylbenzyl | Cyclohexyl | CH$_2$ | 5 | — | |
| 75a | p-tert.-Butylbenzyl | Cyclooctyl | CH$_2$ | 5 | — | |
| 76a | p-(1,1,2-Trimethylpropyl)-benzyl | H | CH$_2$ | 5 | — | |
| 77a | p-(1,1,2-Trimethylpropyl)-benzyl | Cyclooctyl | CH$_2$ | 5 | — | |
| 78a | p-tert.-Butoxybenzyl | H | CH$_2$ | 5 | — | |
| 79a | p-tert.-Butoxybenzyl | 1,2-Dimethyl- | CH$_2$ | 5 | — | |

TABLE 1-continued $$R^1-NH\underset{R^2\diagdown N}{\diagdown}NH-(CH_2)_n-X-(CH_2)_n-NH\underset{N\diagdown R^2}{\diagup}NH-R^1 \cdot HY$$

| Comp. No. | R¹ | R² | X | n | HY | m.p./IR (film) [cm⁻¹] |
|---|---|---|---|---|---|---|
| | | propyl | | | | |
| 80a | p-tert.-Butylbenzyl | H | single bond | 6 | — | |
| 81a | p-tert.-Butylbenzyl | Butyl | single bond | 6 | — | |
| 82a | p-tert.-Butylbenzyl | Cyclohexyl | single bond | 6 | — | |
| 83a | p-tert.-Butoxybenzyl | H | single bond | 6 | — | |
| 84a | p-tert.-Butoxybenzyl | Cyclohexyl | single bond | 6 | — | |
| 85a | Cyclohexyl | H | NMe | 6 | — | |
| 86a | Cyclohexyl | H | N—CH₂Ph | 8 | — | |
| 87a | p-tert.-Butylbenzyl | H | N—Me | 6 | — | |
| 88a | p-tert.-Butylbenzyl | H | N—CH₂—C₆H₄—C(CH₃)₃ (p-tert-butylbenzyl) | 8 | — | |

TABLE 2

$$\left( R^1-\underset{R^2-N}{\overset{H}{N}}\diagdown NH-(CH_2)_n-X-(CH_2)_n-NH\diagdown \underset{N-R^2}{\overset{H}{N}}-R^1 \right) \cdot HY$$

| Comp. No. | $R^1-\underset{R^2-N}{\overset{H}{N}}\diagdown$ (ring) | X | n | HY | m.p./IR (film) [cm⁻¹] |
|---|---|---|---|---|---|
| 1b | 2-methyl-imidazoline | NH | 6 | HCl | 195° C. |
| 2b | 2-methyl-imidazoline | NH | 6 | CH₃COOH | 3165, 3051, 2933, 2858, 1679, 1560, 1471, 1402, 1286 |
| 3b | 2-methyl-imidazoline | NH | 6 | C₂H₂O | 100° C. |
| 4b | 2-methyl-imidazoline | NH | 6 | — | |
| 5b | 2-methyl-tetrahydropyrimidine | NH | 6 | HI | 3225, 2930, 1643, 1316 |
| 6b | 2,5,5-trimethyl-tetrahydropyrimidine | NH | 6 | — | |

TABLE 2-continued $$R^1-N(H)-C(=N-R^2)-NH-(CH_2)_n-X-(CH_2)_n-NH-C(=N-R^2)-N(H)-R^1 \cdot HY$$

| Comp. No. | R¹-N(H)-C(=N-R²) group | X | n | HY | m.p./IR (film) [cm⁻¹] |
|---|---|---|---|---|---|
| 7b | 2-methyl-5-tert-butyl tetrahydropyrimidine | NH | 6 | — | |
| 8b | 2-methyl diazocane with ethyl/propyl substituent | NH | 6 | — | |
| 9b | 2-methyl imidazoline | NH | 8 | — | |
| 10b | 2-methyl tetrahydropyrimidine | NH | 8 | HI | 3218, 2926, 2854, 1643, 1316 |
| 11b | 2-methyl tetrahydropyrimidine | NH | 8 | HCl | 3308, 3236, 3160, 3057, 2929, 2853, 2812, 1654, 1634, 1314 |
| 12b | 2-methyl tetrahydropyrimidine | NH | 8 | $CH_3COOH$ | 3227, 3160, 2927, 2854, 1667, 1567, 1441, 1398, 1318 |
| 13b | 2-methyl tetrahydropyrimidine | NH | 8 | $C_2H_2O_4$ | 140° C. |
| 14b | 2-methyl tetrahydropyrimidine | NH | 8 | — | |
| 15b | 2-methyl-dimethyl tetrahydropyrimidine | NH | 8 | — | |

TABLE 2-continued $$\left(\begin{matrix}R^1-N{\overset{H}{\diagdown}}\\ R^2-N{\diagup}\end{matrix}\right)\!\!C-NH-(CH_2)_n-X-(CH_2)_n-NH-C\!\!\left(\begin{matrix}{\overset{H}{\diagup}}N-R^1\\ {\diagdown}N-R^2\end{matrix}\right)\cdot HY$$

| Comp. No. | $\begin{matrix}R^1-N{\overset{H}{\diagdown}}\\ R^2-N{\diagup}\end{matrix}C-$ | X | n | HY | m.p./IR (film) [cm$^{-1}$] |
|---|---|---|---|---|---|
| 16b | 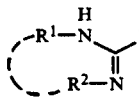 | NH | 8 | — | |
| 17b | 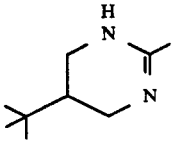 | NH | 8 | — | |
| 18b | 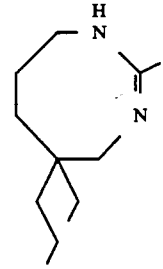 | single bond | 5 | — | |
| 19b | 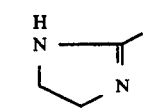 | single bond | 5 | — | |
| 20b | 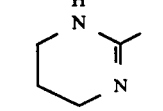 | single bond | 5 | — | |
| 21b | 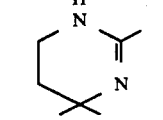 | single bond | 5 | — | |
| 22b | 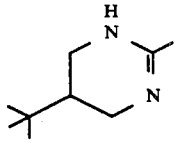 | single bond | 5 | — | |
| 23b | 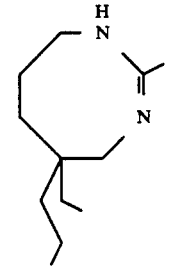 | CH$_2$ | 5 | — | |

TABLE 2-continued
$$\left(R^1-N\atop R^2-N\right)\!\!-\!\!NH-(CH_2)_n-X-(CH_2)_n-NH-\!\!\left(N-R^1\atop N-R^2\right)\cdot HY$$
| Comp. No. | $\left(R^1-N\atop R^2-N\right)$ | X | n | HY | m.p./IR (film) [cm$^{-1}$] |
|---|---|---|---|---|---|
| 24b | 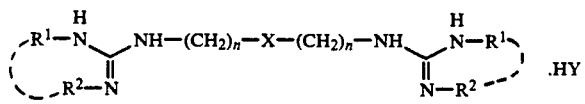 | CH$_2$ | 5 | — | |
| 25b | 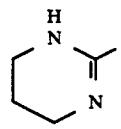 | CH$_2$ | 5 | — | |
| 26b | 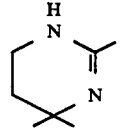 | CH$_2$ | 5 | — | |
| 27b | 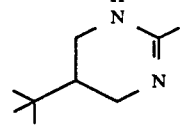 | CH$_2$ | 5 | — | |
| 28b | 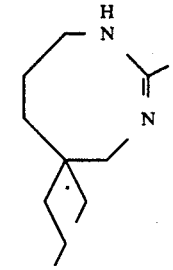 | single bond | 6 | — | 3284, 2916, 2849, 1637, 1612, 1556, 1470, 1262 |
| 29b | 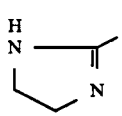 | single bond | 6 | HJ | 197° C. |
| 30b |  | single bond | 6 | HCl | 3290, 3142, 3063, 3001, 2984, 2926, 2862, 2853, 1674, 1590 |
| 31b | 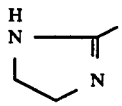 | single bond | 6 | CH$_3$COOH | 2926, 2854, 1677, 1560, 1396, 1285 |
| 32b | 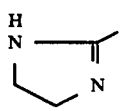 | single bond | 6 | — | 156–158° C. |

TABLE 2-continued
$$\begin{pmatrix} R^1-N \\ R^2-N \end{pmatrix} NH-(CH_2)_n-X-(CH_2)_n-NH \begin{pmatrix} N-R^1 \\ N-R^2 \end{pmatrix} \cdot HY$$
| Comp. No. | 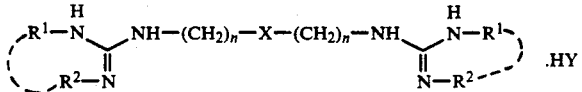 | X | n | HY | m.p./IR (film) [cm$^{-1}$] |
|---|---|---|---|---|---|
| 33b | 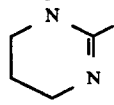 | single bond | 6 | HCl | 3214, 3067, 2926, 2854, 1646, 1317 |
| 34b | 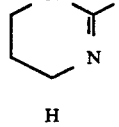 | single bond | 6 | HI | 3217, 2925, 2853, 1642, 1315 |
| 35b | 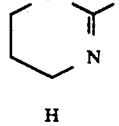 | single bond | 6 | CH$_3$COOH | 3231, 2928, 2855, 1660, 1558, 1275 |
| 36b | 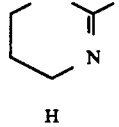 | single bond | 6 | C$_2$H$_2$O$_4$ | 140–142° C. |
| 37b | 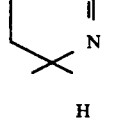 | single bond | 6 | — | |
| 38b | 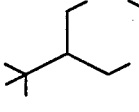 | single bond | 6 | — | |
| 39b | 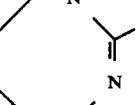 | single bond | 6 | — | |
| 40b |  | N—Me | 8 | — | |
| 41b | 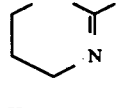 | 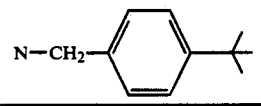 | 6 | — | |

The compounds are suitable as fungicides.

The fungicidal compounds and the agents containing them can be applied, for example, in the form of directly sprayable solutions, powders, suspensions, including concentrated aqueous, oily or other suspensions or dispersions, emulsions, oily dispersions, pastes, dusts, broadcasting agents or granules by spraying, atomizing, dusting, broadcasting or watering. The modes of application depend on the purposes for which they are used; they should ensure in all cases the finest possible dispersion of the active ingredients according to the invention.

The plants are normally sprayed or dusted with the active ingredients or the seeds of the plants are treated with the active ingredients.

The formulations are prepared in a conventional manner, for example by diluting the active ingredient with solvents and/or carriers, if desired using emulsifiers and dispersants, it being possible when water is used as diluent also to add organic solvents as cosolvents. Auxiliaries suitable for this purpose are essentially: solvents such as aromatic compounds (e.g. xylene), chlorinated aromatic compounds (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers such as natural rock meals (e.g. kaolins, aluminas, talc, chalk) and synthetic rock meals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignin sulfite waste liquors and methylcellulose.

Suitable surfactants are alkali metal, alkaline earth metal and ammonium salts of aromatic sulfonic acids, e.g. lignin-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, products of the condensation of sulfonated naphthalene and its derivatives with formaldehyde, of naphthalene or of naphthalenesulfonic acids with phenol and formaldehyde, polyoxyethylene octylphenol ethers, ethoxylated isooctyl-, octyl- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignin sulfite waste liquors or methylcellulose.

Powders, dusts and broadcasting agents can be prepared by mixing or milling together the active substances with a solid carrier.

Granules, e.g. coated, impregnated or homogeneous granules, can be prepared by binding the active ingredients to solid carriers. Solid carriers are mineral earths such as silica gel, silicic acids, silicates, talc, kaolin, limestone, lime, chalk, bole, loess, clay, dolomite, diatomaceous earth, calcium and magnesium sulfate, magnesium oxide, milled synthetic materials, fertilizers such as ammonium sulfate, ammonium phosphate, ammonium nitrate, urea and vegetable products such as cereals meal, bark, wood and nutshell meals, cellulose powder or other solid carriers.

Examples of such formulations are:

I. a solution of 90 parts by weight of compound No. 12a and 10 parts by weight of N-methyl-α-pyrrolidone, which is suitable for use in the form of very small droplets;

II. a mixture of 20 parts by weight of compound No. 14a, 80 parts by weight of xylene, 10 parts by weight of the adduct of 8 to 10 moles of ethylene oxide and 1 mole of oleic acid N-monoethanolamide, amide, 5 parts by weight of calcium dodecylbenzenesulfonate, 5 parts by weight of the adduct of 40 moles of ethylene oxide and 1 mole of castor oil; the solution is finely dispersed in water;

III. an aqueous dispersion of 20 parts by weight of compound No. 30b, 40 parts by weight of cyclohexanone, 30 parts by weight of isobutanol, 20 parts by weight of the adduct of 40 moles of ethylene oxide and 1 mole of castor oil;

IV. an aqueous dispersion of 20 parts by weight of compound No. 31b, 25 parts by weight of cyclohexanol, 65 parts by weight of a mineral oil fraction of boiling point 210 to 280° C. and 10 parts by weight of the adduct of 40 moles of ethylene oxide and 1 mole of castor oil;

V. a mixture, milled in a hammer mill, of 80 parts by weight of compound No. 35b, 3 parts by weight of sodium diisobutylnaphthalene-α-sulfonate, 10 parts by weight of the sodium salt of a ligninsulfonic acid from a sulfite waste liquor and 7 parts by weight of powdered silica gel; the mixture is finely dispersed in water to give a sprayable composition;

VI. an intimate mixture of 3 parts by weight of compound No. 31b and 97 parts by weight of finely divided kaolin; this dust contains 3% by weight of active ingredient;

VII. an intimate mixture of 30 parts by weight of compound No. 12a, 92 parts by weight of powdered silica gel and 8 parts by weight of liquid paraffin which has been sprayed onto the surface of this silica gel; this preparation confers good adhesion on the active ingredient;

VIII. a stable aqueous dispersion of 40 parts by weight of compound No. 14a, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of compound No. 14a, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a paraffin mineral oil.

The compounds have excellent activity against a wide spectrum of phytopathogenic fungi, especially from the Ascomycetes and Basidiomycetes classes. Some of them have systemic activity and can be employed as leaf and soil fungicides.

They have particular importance for controlling a large number of fungi on various crop plants such as wheat, rye, barley, oats, rice, corn, grass, cotton, soybean, coffee, sugar cane, grapevines, fruit and ornamental plants and vegetable crops such as cucumbers, beans and gourds, as well as the seeds of these plants.

The compounds are applied by treating the fungi or the seeds, plants, materials or soil to be protected from fungal attack with a fungicidally effective amount of the active ingredients. Application takes place before or after infection of the materials, plants or seeds by the fungi.

The compounds are suitable for controlling the following specific plant diseases:

*Erysiphe graminis* (powdery mildew) on cereals,
*Erysiphe cichoracearum* and *Sphaerotheca fuliginea* on gourds,
*Podosphaera leucotricha* on apples,
*Uncinula necator* on grapevines,
*Puccinia* species on cereals,
*Rhizoctonia* species on cotton and lawns,
*Ustilago* species on cereals and sugar cane,
*Venturia inaequalis* (scab) on apples,
*Helminthosporium* species on cereals,
*Septoria nodorum* on wheat,
*Botrytis cinerea* (gray mold) on strawberries and grapevines,
*Cercospora arachidicola* on peanuts,
*Pseudocercosporella herpotrichoides* on wheat and barley,
*Pyricularia oryzae* on rice,
*Phytophthora infestans* on potatoes and tomatoes,
*Fusarium* and *Verticillium* species on various crops,
*Plasmopara viticola* on grapevines,
*Alternaria* species on vegetables and fruit.

The novel compounds can also be used to protect materials (wood), e.g. against *Paecilomyces variotii*.

The fungicidal agents generally contain from 0.1 to 95, preferably from 0.5 to 90, % by weight of active ingredient.

The application rates depend on the nature of the desired effect and are from 0.02 to 3 kg of active ingredient per ha.

Generally required for treating seeds is from 0.001 to 50 g, preferably 0.01 to 10 g, of active ingredient per kilogram of seeds.

The fungicidal agents according to the invention can contain other active ingredients, e.g. herbicides, insecticides, growth regulators, fungicides or fertilizers. Mixing with fungicides in many cases results in an extension of the range of fungicidal activity. Use Example Used for comparison was the active ingredient guazatine triacetate (A) disclosed in GB 1 114 155.

Activity on downy mildew of grapevines

Leaves of pot grapevines of the Müller Thurgau variety were sprayed with an aqueous sprayable composition which contained 80% of active ingredient and 20% of emulsifier in dry matter. In order to be able to assess the duration of action of the active ingredients, the plants were placed in a greenhouse for 8 days after the spray deposit had dried. Only then were the leaves infected with a suspension of zoo spores of Plasmopara viticola (downy mildew of grapevines). The grapevines were then placed initially in a chamber saturated with water vapor at 24° C. for 48 hours and then in a greenhouse at from 20° to 30° C. for 5 days. After this time, the plants were placed in the humid chamber for a further 16 hours to increase the rate of sporangiophore discharge. The extent of fungal attack was then assessed on the undersides of the leaves.

The result shows that active ingredients 12a, 14a, 30b and 31b when applied as a 0.025% strength (by weight) sprayable composition have a better fungicidal action (95%) than the known active ingredient A (65%).

We claim:
1. A substituted bisguanidine of the formula I

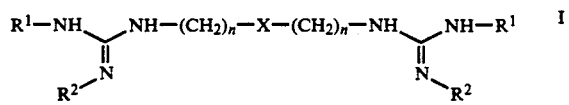

where
$R^2$ is $C_5$-$C_{10}$-alkyl, $C_3$-$C_{10}$-alkenyl, $C_3$-$C_{10}$-alkynyl, $C_1$-$C_8$-alkoxy-$C_2$-$C_8$-alkyl, $C_3$-$C_{10}$-haloalkenyl; or cycloalkyl which has 5-12 carbon atoms in the ring and can carry up to three of the following substituents: hydroxyl, $C_1$-$C_{10}$-alkyl, $C_1$-$C_{10}$-alkoxy, $C_1$-$C_{10}$-haloalkyl and $C_1$-$C_8$-alkoxy-$C_1$-$C_8$-alkyl; or benzyl which can be substituted up to three times by $C_1$-$C_{10}$-alkyl or $C_1$-$C_{10}$-alkoxy, it being possible for these benzyl substituents also to carry a hydroxyl or $C_1$-$C_6$-alkoxy group, or the benzyl is substituted by $C_1$-$C_{10}$-haloalkyl, $R^1$ is benzyl which can be substituted up to three times by $C_1$-$C_{10}$-alkyl or $C_1$-$C_{10}$-alkoxy, it being possible for these benzyl substituents also to carry a hydroxyl or $C_1$-$C_6$-alkoxy group, or the benzyl is substituted by $C_1$-$C_{10}$-haloalkyl, X is $CH_2$, O, a single bond, NH, N-($C_1$-$C_{10}$-alkyl) or N-benzyl whose phenyl can be substituted once to three times by $C_1$-$C_{10}$-alkyl, $C_1$-$C_{10}$-alkoxy, $C_1$-$C_{10}$-haloalkyl or halogen, and n is 5 to 8, and its plant-compatible acid addition salts and its metal complexes.

2. A substituted bisguanidine according to claim 1 wherein X is O.

3. A substituted bisguanidine according to claim 1 wherein X is NH.

4. A substituted bisguanidine according to claim 1 wherein X is N-($C_1$-$C_{10}$-alkyl).

5. A bisguanidine as claimed in claim 1 wherein X is N-benzyl whose phenyl can be substituted one to three times by $C_1$-$C_{10}$-alkyl, $C_1$-$C_{10}$-alkoxy, $C_1$-$C_{10}$-haloalkyl or halogen.

6. A substituted bisguanidine as claimed in claim 1 wherein $R^2$ is $C_3$-$C_{10}$-alkeynl, $C_3$-$C_{10}$-alkynyl, $C_1$-$C_8$-alkoxy-$C_2$-$C_8$-alkyl, $C_3$-$C_{10}$-haloalkenyl or cycloalkyl which has 5-12 carbon atoms in the ring and which can carry up to three of the following substituents: hydroxyl, $C_1$-$C_{10}$-alkyl, $C_1$-$C_{10}$-alkoxy, $C_1$-$C_{10}$-haloalkyl and $C_1$-$C_8$-alkoxy-$C_1$-$C_8$-alkyl.

7. A fungicide containing an effective amount of a bisguanidine of the formula I

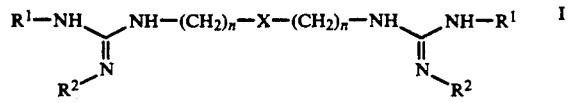

$R^2$ is $C_5$-$C_{10}$-alkyl, $C_3$-$C_{10}$-alkenyl, $C_3$-$C_{10}$-alkynyl, $C_1$-$C_8$-alkoxy-$C_2$-$C_8$-alkyl, $C_3$-$C_{10}$-haloalkenyl; or cycloalkyl which has 5-12 carbon atoms in the ring and can carry up to three of the following substituents: hydroxyl, $C_1$-$C_{10}$-alkyl, $C_1$-$C_{10}$-alkoxy, $C_1$-$C_{10}$-haloalkyl and $C_1$-$C_8$-alkoxy-$C_1$-$C_8$-alkyl; or benzyl which can be substituted up to three times by $C_1$-$C_{10}$-alkyl or $C_1$-$C_{10}$-alkoxy, it being possible for these benzyl substituents also to carry a hydroxyl or $C_1$-$C_6$-alkoxy group, or the benzyl is substituted by $C_1$-$C_{10}$-haloalkyl, R¹ is benzyl which can be substituted up to three times by $C_1$-$C_{10}$-alkyl or $C_1$-$C_{10}$-alkoxy, it being possible for these benzyl substituents also to carry a hydroxyl or $C_1$-$C_6$-alkoxy group, or the benzyl is substituted by $C_1$-$C_{10}$-haloalkyl, X is $CH_2$, O, a single bond, NH, N-($C_1$-$C_{10}$-alkyl) or N-benzyl whose phenyl can be substituted once to three times by $C_1$-$C_{10}$-alkyl, $C_1$-$C_{10}$-alkoxy, $C_1$-$C_{10}$-haloalkyl or halogen, and n is 5 to 8, or salt or its metal complex and a liquid or solid carrier.

8. A process for controlling fungi, which comprises allowing an effective amount of a bisguanidine of the formula I

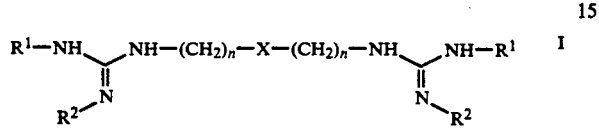

R² is $C_2$-$C_{10}$-alkyl, $C_3$-$C_{10}$-alkenyl, $C_3$-$C_{10}$-alkynyl, $C_1$-$C_8$-alkoxy-$C_2$-$C_8$-alkyl, $C_3$-$C_{10}$-haloalkenyl; or cycloalkyl which has 5-12 carbon atoms in the ring and can carry up to three of the following substituents: hydroxyl, $C_1$-$C_{10}$-alkyl, $C_1$-$C_{10}$-alkoxy, $C_1$-$C_{10}$-haloalkyl and $C_1$-$C_8$-alkoxy-$C_1$-$C_8$-alkyl; or benzyl which can be substituted up to three times by $C_1$-$C_{10}$-alkyl or $C_1$-$C_{10}$-alkoxy, it being possible for these benzyl substituents also to carry a hydroxyl or $C_1$-$C_6$-alkoxy group, or the benzyl is substituted by $C_1$-$C_{10}$-haloalkyl, R¹ is benzyl which can be substituted up to three times by $C_1$-$C_{10}$-alkyl or $C_1$-$C_{10}$-alkoxy, it being possible for these benzyl substituents also to carry a hydroxyl or $C_1$-$C_6$-alkoxy group, or the benzyl is substituted by $C_1$-$C_{10}$-haloalkyl, X is $CH_2$, O, a single bond, NH, N-($C_1$-$C_{10}$-alkyl) or N-benzyl whose phenyl can be substituted once to three times by $C_1$-$C_{10}$-alkyl, $C_1$-$C_{10}$-alkoxy, $C_1$-$C_{10}$-haloalkyl or halogen, and n is 5 to 8, or its salt or metal complex to act on fungi, plants at risk or fungal attack, their habitat or their seed, or on materials.

* * * * *